(12) United States Patent
Visser et al.

(10) Patent No.: US 9,556,092 B2
(45) Date of Patent: Jan. 31, 2017

(54) METHOD AND APPARATUS FOR PROVIDING OXYGENATED HYDROCARBONS

(71) Applicant: GAS TECHNOLOGIES LLC, Walloon Lake, MI (US)

(72) Inventors: Evan Michael Visser, Hull, IA (US); Ian Lawrence Gaffney, Los Gatos, CA (US); Walter Briedenstein, Boyne Falls, MI (US)

(73) Assignee: GAS TECHNOLOGIES LLC, Walloon Lake, MI (US)

(*) Notice: Subject to any disclaimer, the term of this patent is extended or adjusted under 35 U.S.C. 154(b) by 0 days.

(21) Appl. No.: 14/440,948

(22) PCT Filed: Dec. 23, 2013

(86) PCT No.: PCT/US2013/077488
§ 371 (c)(1),
(2) Date: May 6, 2015

(87) PCT Pub. No.: WO2014/100813
PCT Pub. Date: Jun. 26, 2014

(65) Prior Publication Data
US 2015/0299074 A1    Oct. 22, 2015

Related U.S. Application Data

(60) Provisional application No. 61/745,591, filed on Dec. 22, 2012.

(51) Int. Cl.
C07C 27/00 (2006.01)
C07C 29/50 (2006.01)
B01J 19/24 (2006.01)

(52) U.S. Cl.
CPC ............... *C07C 29/50* (2013.01); *B01J 19/24* (2013.01); *B01J 2219/00006* (2013.01); *B01J 2219/00105* (2013.01); *B01J 2219/24* (2013.01)

(58) Field of Classification Search
CPC .................................. C07C 29/50; B01J 19/24
USPC ........................................................ 568/910
See application file for complete search history.

(56) References Cited

U.S. PATENT DOCUMENTS

| | | | |
|---|---|---|---|
| 4,243,613 A | 1/1981 | Brockhaus et al. |
| 4,508,694 A | 4/1985 | Doyle et al. |
| 5,512,599 A | 4/1996 | Hiramatsu et al. |
| 6,136,222 A | 10/2000 | Friesen et al. |
| 6,630,011 B1 | 10/2003 | Baker et al. |
| 7,179,843 B2 | 2/2007 | Bichkov et al. |
| 7,456,327 B2 | 11/2008 | Pawlak et al. |
| 7,578,981 B2 | 8/2009 | Pawlak et al. |
| 7,642,293 B2 | 1/2010 | Pawlak et al. |
| 7,687,669 B2 | 3/2010 | Pawlak et al. |
| 2006/0038283 A1 | 2/2006 | Su et al. |
| 2006/0204413 A1 | 9/2006 | Pawlak et al. |
| 2006/0223892 A1 | 10/2006 | Pawlak et al. |
| 2007/0100005 A1 | 5/2007 | Pawlak et al. |
| 2007/0166212 A1 | 7/2007 | PawlaK et al. |

FOREIGN PATENT DOCUMENTS

| | | | | |
|---|---|---|---|---|
| JP | 07-112945 A | 5/1995 |
| JP | 07-126201 A | 5/1995 |
| JP | 2000-281605 A | 10/2000 |
| JP | 2007-536347 A | 12/2007 |
| RU | 2162460 | 1/2001 |
| RU | 2200731 C1 | 3/2003 |
| RU | WO 2007075178 A1 | * 7/2007 | .......... B01J 19/2415 |
| WO | 2007075178 A1 | 7/2007 |
| WO | 2005108336 A1 | 11/2008 |

OTHER PUBLICATIONS

Karavaev, M.M. et al., Technology of Synthetic Methanol, Moscow, Chemistry 1984, pp. 72-125.
English Translation (45 pgs) of Karavaev, M.M. et al., Technology of Synthetic Methanol, Moscow, Chemistry 1984, pp. 72-125 using Google translate.
Lokhandwala, K. A. et al., "Membrane separation of nitrogen from natural gas: A case study from membrane synthesis to commercial deployment", Journal of Membrane Science, 2010, pp. 270-279.
International Search Report mailed Apr. 21, 2014 for PCT/US2014/030161, Filed Dec. 23, 2013, 4 pgs.

* cited by examiner

*Primary Examiner* — Porfirio Nazario Gonzalez
*Assistant Examiner* — Kofi Adzamli
(74) *Attorney, Agent, or Firm* — Brooks Kushman P.C.

(57) ABSTRACT

A method includes a step of supplying a first heated hydrocarbon-containing gas stream to a reactor. An oxygen-containing gas stream is separately supplied to the reactor to partially oxidize the hydrocarbon-containing gas stream. The oxygen-containing gas is optionally prepared by passing air through one or more membranes to increase the oxygen content. One or more of the desired liquid oxygenated hydrocarbons are condensed and/or separated from the resulting product stream. Non-hydrocarbon gases are selectively removed from the product stream to enrich the gaseous hydrocarbon fraction using a scrubber and/or a membrane. The remaining gaseous hydrocarbon products from the product stream are mixed with a fresh hydrocarbon-containing gas stream after one cycle of the reaction. Characteristically, the process uses at least one membrane to increase oxygen content of the oxygen containing gas and/or to remove non-hydrocarbon gases from the product stream as set forth above.

35 Claims, 1 Drawing Sheet

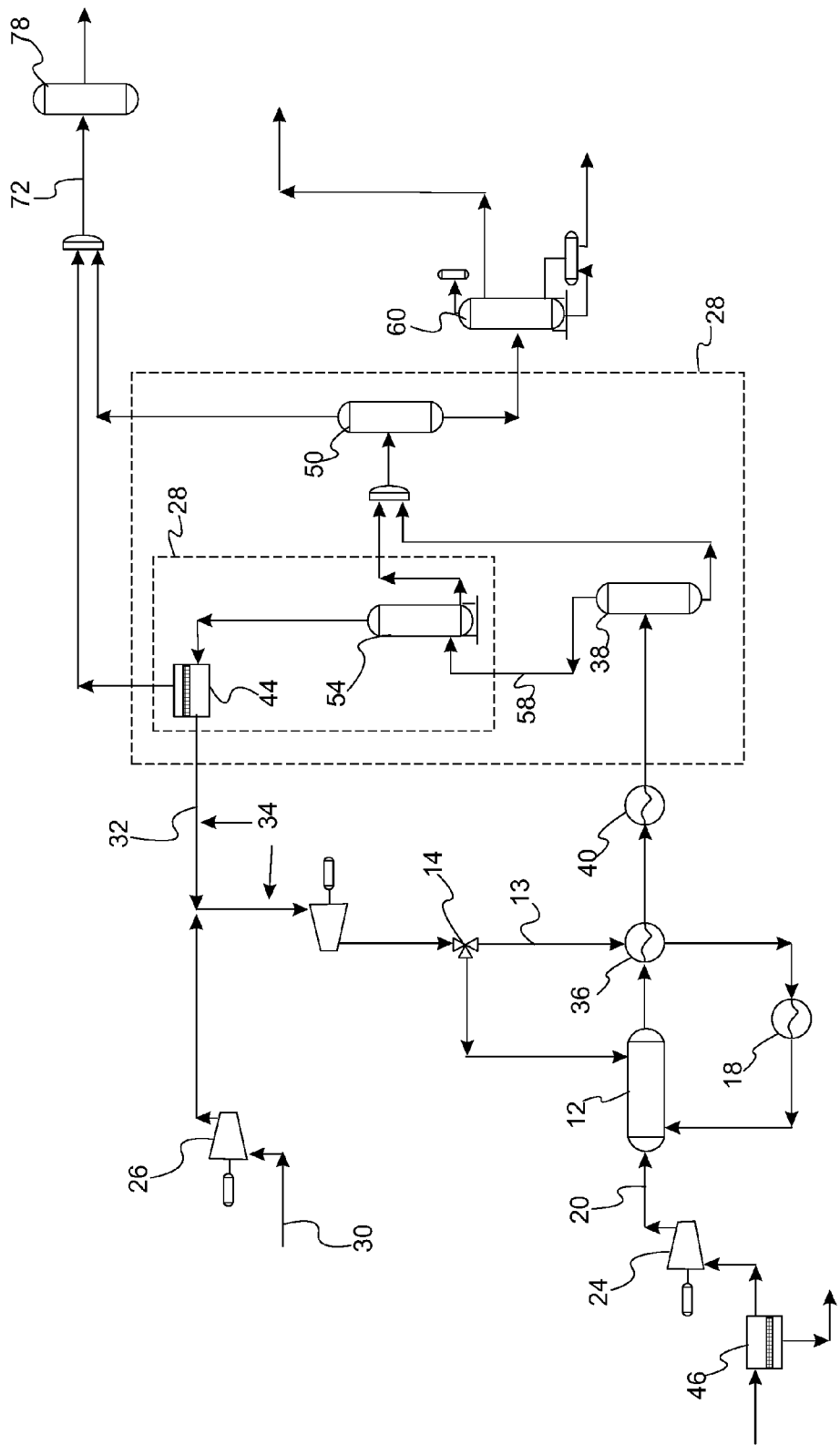

METHOD AND APPARATUS FOR PROVIDING OXYGENATED HYDROCARBONS

CROSS-REFERENCE TO RELATED APPLICATIONS

This application is the U.S. National Phase of PCT Appln. No. PCT/US2013/077488 filed Dec. 23, 2013, which claims the benefit of U.S. provisional application Ser. No. 61/745,591 filed Dec. 22, 2012, the disclosures of which are incorporated in their entirety by reference herein.

TECHNICAL FIELD

The present invention relates to a method and apparatus for producing oxygenated hydrocarbons (especially methanol). More specifically, the embodiments are for converting alkanes, such as methane, ethane, propane and butane, into alkyl oxygenates, and in particular, for direct oxidation (under partial oxidation conditions) of methane (e.g. from natural gas) to methanol and formaldehyde.

BACKGROUND

The current industrial practice for methanol production is a two-step reaction. The first step is the cleaning and reforming of methane (from natural gas) to carbon monoxide and hydrogen. This is followed by a second step consisting of a reaction between carbon monoxide and hydrogen in the presence of a solid catalyst to form methanol. This process is energy-intensive and uneconomical for all but very large scale methanol plants. The present invention relates to a method and apparatus for producing oxygenated hydrocarbons (especially methanol). More specifically, the embodiments are for converting alkanes, such as methane, ethane, propane and butane, into alkyl oxygenates, and in particular, for direct oxidation (under partial oxidation conditions) of methane (e.g. from natural gas) to alcohols and additional oxygenated hydrocarbons.

Various other methods and apparatuses for converting methane into methanol are also known. It is known to carry out a vapor-phase reformation of methane into synthesis gas (mixture of carbon monoxide and hydrogen) with its subsequent catalytic conversion into methanol, as disclosed, for example, in Karavaev M. M., Leonov B. E., et al "Technology of Synthetic Methanol", Moscow, "Chemistry" 1984, pages 72-125. However, in order to realize this process, highly sophisticated equipment is needed to satisfy the high requirements of gas purity. Large quantities of energy are also consumed to obtain the synthesis gas and for its purification, with a significant number of intermittent stages in the process. This complexity makes the process economically unviable for medium and small enterprises with the capacity less than 2,000 tons/day.

Russian Patent No. 2,162,460 includes a source of hydrocarbon-containing gas, a compressor and a heater for compression and heating of this gas, and an oxygen-containing gas with a compressor. It further includes successively arranged reactors with alternating mixing and reaction zones and means to supply the hydrocarbon-containing gas into a first mixing zone of the reactor and the oxygen-containing gas into each mixing zone, a recuperative heat exchanger for cooling of the reaction mixture, a cooler-condenser, a partial condenser for separation of waste gases and liquid products with a subsequent separation of methanol, a pipeline for supply of the waste gas into the initial hydrocarbon-containing gas, and a pipeline for supply of waste oxygen-containing products into the first mixing zone of the reactor. In this apparatus, however, fast withdrawal of heat from the highly exothermic oxidation reaction of the hydrocarbon-containing gas is not achievable because of the inherent limitations of the heat exchanger. This leads to the need for a reduction in the quantity of supplied oxygen-containing gas and, further, it reduces the degree of conversion of the hydrocarbon-containing gas. Moreover, even with the use of oxygen as an oxidizer, it is not possible to provide an efficient recirculation of the hydrocarbon-containing gas due to the rapid increase in the concentration of carbon oxides. A significant part of the supplied oxygen is wasted for oxidation of carbon monoxide into carbon dioxide, which additionally reduces the degree of conversion of the initial hydrocarbon-containing gas to useful products and provides a further overheating of the reaction mixture. As it is necessary to cool these components in the gas-liquid mixture to recover the liquid fraction followed by subsequent heating before returning to the reactor, much energy is wasted. Furthermore, these components are recompressed after each pass through the recycle compressor. Thus, the substantial elimination of non-hydrocarbon components provides an opportunity to reduce operational and capital expenditures.

A further method and apparatus for producing methanol is disclosed in the patent document RU 2,200,731, in which compressed heated hydrocarbon-containing gas and compressed oxygen-containing gas are introduced into mixing zones of successively arranged reactors, and the reaction is performed with a controlled heat pick-up by cooling of the reaction mixture with water condensate so that steam is obtained, and a degree of cooling of the reaction mixture is regulated by parameters of escaping steam, which is used in a liquid product rectification stage.

U.S. Pat. Nos. 7,179,843, 7,456,327, 7,578,981, 7,642,293 and 7,687,669, and Published US patent applications Nos. 20060204413, 20060223892, 200638283, 20070100005 and 20070166212, which are incorporated herein by reference, describe efficient and low-cost methods and apparatuses for the direct partial oxidation of methane to methanol without use of a catalyst. However, because recycle systems are suspect to accumulation of inert gases naturally occurring in the hydrocarbon-gas or in the oxygen containing gas, as well as product gases of the partial oxidation reaction, by selectively removing these fractions from the recycle system efficiencies can be significantly improved and oxygen consumption reduced.

It is observed that the methods and apparatuses can be used with minimal processing of on-shore gas and gas-condensate deposits, as well as integrated with any gas consumer, such as power plants, gas distributing and gas reducing stations, chemical production facilities, etc., or small methane producers (e.g. coal mines, oil production (flares), landfills, farms, etc.).

Accordingly, there exists a need for an improved method and apparatus to permit for safe conversion of hydrocarbon-containing gas to liquids on off-shore rigs, and also for improved efficiencies and simplification to enable a closed cycle system for producing methanol and other oxygenated hydrocarbons.

SUMMARY

It is accordingly an object of the present invention to provide a method and apparatus for producing oxygenated hydrocarbons (especially methanol), which is a further improvement of the existing methods and apparatuses.

In keeping with this object and with others which will become apparent hereinafter, one feature of the present invention is a method for producing oxygenated hydrocarbons, such as methanol. The method includes a step of supplying a first heated hydrocarbon-containing gas stream to a reactor. An oxygen-containing gas stream is separately supplied to the reactor to partially oxidize the hydrocarbon-containing gas stream. The oxygen-containing gas is optionally prepared by passing air through one or more membranes to increase the oxygen content. One or more of the desired liquid oxygenated hydrocarbons are condensed and/or separated from the resulting product stream. Non-hydrocarbon gases are selectively removed from the product stream to enrich the gaseous hydrocarbon fraction using an absorptive scrubber and/or a membrane. The remaining gaseous hydrocarbon products from the product stream are mixed with a fresh, optionally heated, hydrocarbon-containing gas stream after one cycle of the reaction. Characteristically, the process uses at least one membrane to increase oxygen content of the oxygen containing gas and/or to remove non-hydrocarbon gases from the product stream as set forth above. In a refinement, multiple membranes are used in series. In another refinement, multiple membranes are used in parallel. In still other refinement, a first set of membranes are used in parallel simultaneous to a second set of membranes being used in series.

In another embodiment, a method for preparing oxygenated hydrocarbons is provided. The method includes a step of supplying to a reactor a first heated hydrocarbon-containing gas stream. An oxygen-containing gas stream is separately supplied to the reactor to form a reaction mixture. The oxygen-containing gas stream being optionally prepared by passing air through one or more oxygen-enriching membranes to increase oxygen content, to partially oxidize the hydrocarbon-containing gas stream in a partial oxidation reaction. One or more oxygenated hydrocarbons are separated and/or condensed from a product stream. Non-hydrocarbon gases are removed from the product stream to enrich a gaseous hydrocarbon fraction using a scrubber and/or a hydrocarbon-enriching membrane. The remaining gaseous hydrocarbon product from the product stream is mixed with a fresh first heated hydrocarbon-containing gas stream after one reaction cycle. Characteristically, at least one membrane is used to increase oxygen content of the oxygen-containing gas stream and/or to remove non-hydrocarbon gases from the product stream.

In still another embodiment, a method for producing methanol is provided. The method includes a step of supplying to a reactor a first heated hydrocarbon-containing gas stream. An oxygen-containing gas stream is separately supplied to the reactor. Optionally prepared by passing air through one or more membranes to increase oxygen content, to oxidize the hydrocarbon-containing gas stream to form a product stream. one or more oxygenated hydrocarbons including methanol are separated and/or condensed from the product stream. Carbon monoxide and/or carbon dioxide are removed from the product stream comprising one or more oxygenated hydrocarbons using a scrubber and a membrane. Remaining gaseous hydrocarbon product from the product stream are mixed with the first hydrocarbon-containing gas stream after one reaction cycle.

Another feature of the present teachings is an apparatus for producing oxygenated hydrocarbons, such as methanol. The apparatus includes a reactor, a first hydrocarbon-containing gas supply means for supplying into the reactor a heated hydrocarbon-containing gas, means for supplying into the reactor an oxygen-containing gas, optionally one or more membranes to increase the oxygen content of the oxygen-containing gas supplied into the reactor, means for condensing and/or separating one or more of the desired liquid oxygenated hydrocarbons from the resulting product stream, a scrubber and/or a membrane to selectively remove non-hydrocarbon gases from the product stream, and means for mixing the remaining gaseous hydrocarbon product from the product stream with a fresh first heated hydrocarbon-containing gas stream after one cycle of the reaction. Characteristically, the apparatus is provided with at least one membrane.

In another embodiment, a system implementing the method set forth above is provided. The system includes a reactor, a first hydrocarbon-containing gas supply means for supplying into the reactor a heated hydrocarbon-containing gas, a means for supplying into the reactor an oxygen-containing gas, optionally one or more oxygen-enriching membranes to increase oxygen content of the oxygen-containing gas supplied into the reactor, a means for separating and/or condensing one or more liquid oxygenated hydrocarbons from a product stream, a scrubber and/or a hydrocarbon-enriching membrane to remove non-hydrocarbon gases from the product stream, and a means for mixing remaining gaseous hydrocarbon product from the product stream with a fresh first heated hydrocarbon-containing gas stream after one reaction cycle, the system having at least one membrane.

As can be seen, in accordance with the present teachings, a heated hydrocarbon-containing gas stream and oxygen-containing gas are supplied into a reactor, where a gas phase oxidation of the hydrocarbon-containing gas is performed at elevated temperature and pressure in the reaction zone. The oxygen-containing gas may preferably be prepared by passing air through one or more membranes to increase the oxygen content. The reaction mixture is cooled and separated into gas and liquid product. The gas may be scrubbed and/or passed through a membrane to selectively remove non-hydrocarbon gases and then returned to the heated hydrocarbon-containing gas stream prior to a second cycle of the reaction.

The present invention is more efficient and cost-effective than the prior art processes. First, the PSA/VSA/cryo-oxygen unit can be replaced in part or in whole with a significantly lower cost membrane to enrich the air entering the system. A membrane may also be present within the recycle loop, with or without a scrubber, to further remove nitrogen and potentially other non-hydrocarbon gases such as carbon oxides and/or hydrogen. A further feature of the present invention is the use of separated carbon oxides and hydrogen for the synthesis of valuable oxygenated hydrocarbons. By these means, carbon efficiency is further enhanced. It may be necessary, when solid state membranes are used, to remove the liquid oxygenated hydrocarbon product by scrubbing out the liquid and/or by condensation followed by separating the liquids before contact is made with the membrane. This may prevent any fouling of the membrane which might otherwise occur. On the other hand, liquid membranes may potentially be used without the scrubbing or condensation/separation steps.

Fresh hydrocarbon-containing feed gas may also be introduced into the recycle stream prior to contact with the membrane. Whether the feed is introduced before or after the selective non-hydrocarbon removal system (membrane with or without additional scrubbers) will depend on the composition of the gases and the selectivity of the non-hydrocarbon removal system. A pure hydrocarbon feed will dilute the non-hydrocarbon gases in the recycle stream and decrease their partial pressures. Some feeds, however, will contain gases that are separable by the scrubbing/membrane system. For example, refinery, petrochemical, and coke production gases typically contain olefins, hydrogen, and/or carbon monoxide which would be advantageously separated by the membrane/scrubbing system and therefore should be introduced prior to contact with the membrane/scrubber but after the reactor in the recycle loop.

The apparatus also has a mechanism for supplying into the reactor a non-oxidizing coolant to be directly mixed with a mixture of said heated hydrocarbon containing gas and said oxygen containing gas at a later stage of the reaction to inhibit the decomposition of formaldehyde. The coolant functions to inhibit the oxidation or decomposition of the formaldehyde product as well as regulate the temperature of the product gas prior to entering the cross exchanger. Unreacted hydrocarbon gas is then processed to separate liquid products and selectively remove non-hydrocarbon gases before being recycled back into the hydrocarbon-containing gas stream.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 1 shows a process flow diagram for one example of the method and apparatus according to the invention.

DETAILED DESCRIPTION

As required, detailed embodiments of the present invention are disclosed herein; however, it is to be understood that the disclosed embodiments are merely exemplary of the invention that may be embodied in various and alternative forms. The FIGURE is not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The following definitions and non-limiting guidelines must be considered in reviewing the description of this invention set forth herein.

The headings (such as "Background" and "Summary") and any sub-headings used herein are intended only for general organization of topics within the disclosure of the invention and are not intended to limit the disclosure of the invention or any aspect thereof. In particular, subject matter disclosed in the "Background" may include aspects of technology within the scope of the invention, and may not constitute solely a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations of the stated of features.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in compositions, materials, devices, and methods of this invention.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

The embodiments relate to direct oxygenation conversion of at least one hydrocarbon into at least one oxygenated hydrocarbon. The direct oxygenation conversion of methane into methanol and oxygenates is a focal conversion goal of the technology.

In one embodiment, an improved, compact, reactor system for executing the overall reaction for the partial oxidation of methane and/or natural gas to oxygenated hydrocarbons is provided. In overview, the system allows for the passing of a mixture of natural gas and oxidant through a heated, continuous flow reactor system under conditions to optimize the formation of methanol, and to manipulate the reactor temperature, total pressure, and fuel (e.g., without limitation, natural gas) to oxidant ratio to control the relative amounts of reaction products. The reaction is a partial oxidation of a hydrocarbon fuel, such as natural gas, by an oxidant, such as oxygen, air, or other suitable oxygen-containing compound (preferably oxygen in air or, most preferably, oxygen). The mixture contains a substantial excess of fuel (e.g., without limitation, natural gas) to prevent over oxidation to undesired products such as carbon dioxide and water. Advantageously, the system is suitable for small, isolated natural gas sources (stranded gas).

With reference to FIG. 1, an apparatus for producing oxygenated hydrocarbons, such as methanol, is provided. The improvements of the present embodiment regarding the incorporation of selective membranes are applicable to the systems and methods set forth in U.S. Pat. Nos. 7,179,843, 7,456,327, 7,578,981, 7,642,293 and 7,687,669, and Published US patent applications Nos. 20060204413, 20060223892, 200638283, 20070100005 and 20070166212, the entire disclosures of which are hereby incorporated by reference. System 10 includes reactor 12 for a gas phase oxidation of the hydrocarbon-containing gas. A hydrocarbon-containing gas stream 13 (flowing through valve 14 and heater 18) and an oxygen-containing gas stream 20 are introduced into reactor 12. In a refinement, the hydrocarbon-containing gas stream 13 includes one or more $C_{1-5}$ alkanes (e.g., methane, ethane, propane, etc.). Typically, hydrocarbon-containing gas stream 13 is heated. It should be appreciated that such heating may be provided by the action of a compressor on the hydrocarbon-containing gas. In a refinement, the oxygen-containing gas stream entering reactor 12 comprises between 20 volume % and 100 volume % oxygen. In another refinement, the oxygen-containing gas stream entering the reactor 12 includes less than 80 volume % nitrogen. As explained in detail below, the oxygen-containing gas preferably has greater than 30 volume % oxygen content, and more preferably greater than 80% oxygen content, to reduce the accumulation of inert gases in the recycle loop. The reactor 12 further optionally receives a quenching cold hydrocarbon-containing gas stream from valve 14 for reducing the temperature of the reaction products during operation of the apparatus.

The reactor 12 is in fluid communication with a compressor 24 for supply of compressed oxygen-containing gas. Pressure of the raw hydrocarbon-containing gas is also increased using a compressor 26 for the supply of compressed gas. Section 28 represents a device or set of devices that is (are) configured to selectively separate non-hydrocarbon gases and products from a hydrocarbon-containing recycle gas component. In particular, the raw hydrocarbon-containing gas is mixed with cleaned hydrocarbon gas from the non-hydrocarbon selective removal unit 30 depicted as recycle loop 32. In a refinement, non-hydrocarbon selective removal unit 30 is a membrane/scrubber system The raw hydrocarbon-containing gas and/or the cleaned hydrocarbon gas from the non-hydrocarbon selective removal unit 30 are heated by the hot reaction product gases in the cross exchanger 34. The preheater 18 serves to further heat the hydrocarbon-containing stream during start up. In the event that the raw hydrocarbon-containing gas stream 31 has a substantial content of non-hydrocarbon gases, this stream can be introduced into the recycle loop 32 downstream of the condenser 38 and prior to entry of the non-hydrocarbon selective removal unit 30 for removal of said non-hydrocarbon gases. The apparatus has a heat exchange device 34 for cooling the reaction product stream mixture and heating the reactant stream mixture. An additional cooling device 40 cools the product stream before entering the partial condenser 38.

In operation, the raw hydrocarbon-containing gas stream with a methane content, for example, up to 99%, and the reduced hydrocarbon product stream are supplied from an installation for preparation of gas or any other source to the heater 18, in which it is heated to temperature 430-470° C. The heated hydrocarbon-containing gas is then supplied into reactor 12. Compressed oxygen enriched air with pressure, for example, of 7-8 MPa and with a ratio of about 20% to about 100% oxygen, is supplied by the compressor 24 and also into reactor 12. Oxidation of methane to methanol or methanol and formaldehyde takes place in reactor 12. To limit the amount of nitrogen within the system 10, for example, to less than about 30% to about 40%, or reduce the nitrogen-removal demand of membrane unit 44, the configuration of the membrane unit 46 may be modified to provide oxygen of greater purity and thus reduce the amount of nitrogen in the system. In this regard, membrane unit 44 includes an oxygen-enriching membrane.

An optional second stream of a lower temperature (e.g. cold) coolant than the gases fed via the cross exchanger 40 and the heater 18 to the reactor 12 may be supplied into reactor 12. This stream is regulated by a valve 14. This cold stream can be, for example, composed of a raw hydrocarbon stream, a recycled stream, or a portion or combination of the two. The coolant functions to reduce the temperature of the partially oxidized methane to reduce the continued oxidation or decomposition of any formed formaldehyde. The coolant can also control heat transfer over cross exchanger 34. By introduction of the coolant, such as a cold hydrocarbon-containing gas, the temperature of the reaction is reduced by at least 30° C. within the reaction vessel, for example by 30-90° C. In a refinement, a second hydrocarbon-containing gas stream is supplied to the reactor downstream of the first heated hydrocarbon-containing gas stream and the oxygen-containing gas stream at a temperature below that of the first heated hydrocarbon-containing gas stream. In a refinement, the second hydrocarbon-containing gas stream includes one or more $C_{1-5}$ alkanes (e.g., methane, ethane, propane, etc). In a further refinement, the second hydrocarbon-containing gas stream is supplied to the reactor at a temperature of 0° C. to 100° C. Advantageously, the second hydrocarbon-containing gas stream is adjusted to mitigate decomposition of formaldehyde in the reactor.

In partial condenser 38, water and liquid oxygenates are separated from a gaseous mixture of hydrocarbons as well as non-hydrocarbon gases such as nitrogen, hydrogen, hydrogen sulfide, carbon monoxide and carbon dioxide. The partial condenser 38 is preferably isobaric, as opposed to isothermal, to avoid pressure losses.

Processing of the liquid streams first includes a flash drum 50 for removal of dissolved gases in the liquids followed by a stripper column 60 in which light alcohols are separated from aldehydes and water. Aldehydes, higher alcohols and water exit the bottom of column 60 in stream 3, which may then be further processed for purification of specific fractions and/or utilization of these products to produce higher value products.

The reaction mixture is supplied into the heat exchanger 34 for transfer of heat to the reactor input stream from the reaction mixture exiting the reactor, and, after further cooling, is supplied to the partial condenser 38. Separation of the mixture into high and low volatility components (dry gas and raw liquid, respectively) is performed in the partial condenser 38, in which aldehydes are also recovered. The dry gas is forwarded to non-hydrocarbon selective removal unit 30 (membrane or membrane and scrubber), while the raw liquids from the condenser 38 are supplied to the flash drum 50.

To minimize the buildup of undesirable non-hydrocarbon gases in the recycle loop, an air separation membrane 46 (i.e., a hydrocarbon-enriching membrane) may separate nitrogen from oxygen to provide an oxygen-rich stream 20. In particular, air separation membrane 46 is used to increase the efficiency of the present process of system 10 by providing oxygen at purities higher than that of atmospheric oxygen (21% volume oxygen, 78% volume nitrogen, 1% volume argon). The membrane is used in preference to means such as pressure-swing adsorption (hereinafter "PSA"), vacuum swing adsorption (hereinafter "VSA") or cryogenic separations, all of which are expensive from both capital and operational perspectives. Membrane 44 provides selective non-hydrocarbon removal to prevent nitrogen buildup in the recycle loop 32.

Typically, air is passed through separation membrane 46 to enrich the oxygen content, for example, by removing at least a portion of the nitrogen present. Suitable membranes for this purpose include ceramic ion transport membranes composed of metal oxides such as aluminum oxide and titanium oxide, which are often capable of generating oxygen at high purities. Zirconia-based oxygen separation membrane materials have also shown good chemical stability and mechanical properties. In another variation, separation membrane 46 includes polymers such as polyimides in order to enhance the oxygen content.

In such systems, oxygen is selectively permeated across the membrane to form a low pressure oxygen enriched permeate stream and a high pressure nitrogen enriched retentate stream. Common purities for a single membrane enrichment system range from 35 to 45 volume percent oxygen. The degree of enrichment depends on parameters such as flow rate and differential pressure over the membrane. Multiple membrane systems with recycle are technically feasible although recompression costs and oxygen recovery must be taken into consideration. Current common practice is to utilize such membranes as nitrogen generation units for purging and blanketing purposes. Therefore, these membranes are widely available and at a low cost. It is also feasible to use a membrane in combination with a cryogenic or adsorption based ASU in order to reduce capital costs and provide oxygen at an intermediate purity such as 45-80 volume percent. It should be appreciated that the system of the present embodiment may be coupled to a nitrogen producing facility that vents oxygen gas thereby providing a source of oxygen for producing oxygenates.

As set forth above, section 28 represents a device or set of devices that are configured to selectively separate non-hydrocarbon gases and products from a hydrocarbon-containing recycle gas component. In particular, non-hydrocarbon selective removal unit 30 represents the device(s) configured to selectively remove non-hydrocarbon gases from the recycle loop 32. Section 30 can take the form of a membrane separation unit 44 alone or integrated with a scrubber as represented by vessel 54. In a refinement, non-hydrocarbon selective removal unit 30 is used to regulate the percentage of non-hydrocarbon gases in the recycle loop consisting of nitrogen, hydrogen, hydrogen sulfide carbon monoxide and carbon dioxide. In this regard, it should be appreciated that nitrogen must be removed to prevent the buildup in the recycle loop 32. In previous practice, the only cost effective method to remove nitrogen was by purging a portion of the recycle gas stream. Nitrogen removal without a membrane is especially problematic. Options include pressure sing adsorption (PSA), cryogenic means, and possibly reactive scrubbing should appropriate solvents be developed in the future. PSA is impractical as a means of nitrogen removal as the operational costs are currently prohibitive with the low conversion, high recycle characteristics of the direct partial oxidation process. Cryogenic nitrogen removal also requires excessive operational costs to achieve the temperatures needed for separation. An example of a nitrogen-absorbing technology that is used in the present embodiment to increase the oxygen content of the oxygen containing gas is provided by U.S. Pat. No. 6,136,222 which describes a nitrogen-absorbing transition metal complex using various ligands such as organophosphine ligands. Such a solution acts as the absorbent in a counter-current rectification column employed to scrub the recycle gas, although this requires on-stream absorbent regeneration and is intolerant of high levels of CO and $O_2$ Section 28 includes non-hydrocarbon selective removal unit 30 which functions to remove non-hydrocarbon gases that are both by-products of the partial oxidation reaction and impurities introduced via the feed gas and/or oxygen containing gas streams. The membrane unit 44 functions to remove nitrogen, hydrogen and/or carbon oxides. Integration with the scrubber 54 may also be utilized for removal of such gases and of other impurities, including sulfur-containing compounds which may potentially poison the membrane. In this regard, the scrubber 54 uses both water and methanol at between about 7 to about 8 MPa pressure and between about 0° C. and about 50° C. to absorb carbon dioxide and hydrated formaldehyde. Once a portion of the non-hydrocarbon gas is removed to prevent excessive buildup, the reduced stream of hydrocarbon gas is recycled by mixing the reduced stream with the raw hydrocarbon-containing gas stream either before or within the reactor by the quench, as desired. If necessary, as in the case of excessive impurities in the feed gas, this feed gas may be combined with the recycle gas after exiting the condenser 38 and before entering non-hydrocarbon selective removal unit 30, in stream 58. The raw hydrocarbon and reduced streams, individually or in combination, are then inputted into reactor 12 after being heated by heat exchanger 34 and heater 18 as previously described. Stripping column 60 is used to separate alcohols (light-key component) from water and hydrated formaldehyde.

For selective removal of carbon monoxide by scrubber 54, a number of patents describe the use of a CuCl CO complexing solution. To date, only the Cosolv process has been commercialized. Toluene selectively absorbs methane at the pressures employed in the present invention. Furthermore, corrosivity issues and incompatibility would prohibit the usage of this technology in the present apparatus. Copper (I) is unstable and has a tendency to disproportionate into elemental copper and Cu(II), thereby degrading the solvent. As an example, U.S. Pat. No. 4,508,694 provides a solution to the problem of disproportionation in part by usage of a stabilizing agent in addition to a fluorinated acetoacetonate. The halogenated acetoacetonate complexes the CO with CuCl in a counter current rectification column. Drawbacks include the expense of and difficulty of synthesis of the absorbent as well as high methane solubility for many of the named solvents which stabilize the system. Future selenium based solvents could be employed which would be able to undergo carbonylation.

Utilization of at least one membrane for selective removal of non-hydrocarbon gases in the recycle loop 32, especially carbon monoxide, carbon dioxide, hydrogen sulfide, hydrogen, and nitrogen, would permit for increased efficiencies as well as utilization of less concentrated oxygen sources. In many membrane materials, CO behaves much like $N_2$ in terms of selectivity and permeability. Membranes for separation of carbon dioxide from natural gas have been available since the 1980's and are typically composed of cellulose acetate, polyimides and perfluoropolymers. Hydrogen separation membranes include dense metals, nano-porous inorganic materials, organic polymers and dense ion transport membranes based on proton conducting materials; composites consisting of combinations of these main material groups are also becoming more common.

Suitable membrane assemblies for removal of non-hydrocarbon gases from the recycle system would ideally offer $N_2/CH_4$ selectivities greater than 1 so as to perform the same carbon dioxide removal function of an absorbent based scrubbing system. Furthermore, $CO_2$ and $H_2$ selectivities should be much higher than methane. Loss of pressure over these membranes must be minimal so as to minimize recompression costs in the recycle system. Furthermore, the membrane should have a MAWP of greater than 6 MPa to accommodate typical operating conditions of the recycle system.

Although not highly selective for nitrogen, the nitrogen selectivity of some nitrogen selective membrane materials over methane is greater than 2. These membrane materials also possess a carbon dioxide selectivity over methane of greater than 20. This membrane module permits for greater selectivity as an alternative to a traditional crude purge stream. The resulting permeate stream will contain a substantial portion of methane, yet would be enriched in non-hydrocarbon gases such that it would perform the same function as a purge gas stream with increased selectivity for the non-hydrocarbon gases, so that the selective purge steam may still be used as potential fuel source or feedstock for additional chemical processing.

Although the main value provided therein is in separating the especially problematic nitrogen and CO from hydrocarbons in the recycle system, these membranes also separate other non-hydrocarbon gases such as carbon dioxide, hydrogen, and hydrogen sulfide with high selectivity on the permeate side of the membrane. When left in the recycle system, these non-hydrocarbon gases inhibit the partial oxidation reaction, but when removed can be further utilized to enhance the overall yield of oxygenated hydrocarbon products.

Another concern is the buildup of carbon dioxide which, to date, has been removed by either an absorption process or purge stream. Carbon dioxide can build up as follows: under a single pass, a portion normally of less than 60% by volume depending on the recycle ratio and oxygen to hydrocarbon ratio, of the methane is oxidized to carbon monoxide by a portion of the input oxygen source. After subsequent passes, a portion of this carbon monoxide, if not removed, is further oxidized to carbon dioxide by additional input oxygen. This increases the demand for valuable oxygen. Further oxygen may be inappropriately consumed if hydrogen remains in the cycle as it would selectively convert to water after one pass through the reactor. Therefore, prior to the present invention, the partial oxidation process of hydrocarbon mixtures such as natural gas to liquid oxygenates was not as efficient as desired due to the extraneous consumption of oxygen and the unwanted generation of carbon oxides which reduced yields of the desired oxygenated hydrocarbons.

The non-hydrocarbon gas fraction removed from the recycle loop may be further processed in a reactor 70 for the generation of higher valued products, as further described below. In another refinement, the one or more separated non-hydrocarbon gases are converted to hydrocarbon which may be used as part of the first hydrocarbon-containing gas stream.

When an absorption scrubber 54 is used together with the membrane unit 44, modification of the flow rate of the absorbent or the operating temperature of the scrubber column can be used to meet the minimum absorption requirements. If it is desirable to operate at extremely low absorbent flow rates, then a lower temperature can be utilized, as occurs for many physical solvents such as those containing methanol for example. It should be appreciated that typically, the scrubber's absorbent reacts with one or more non-hydrocarbon gases in a reversible reaction. If it is desirable to operate at ambient temperatures or temperatures achievable via typical cooling water, then a high flow rate can be utilized, for example, ten times that of the flow rate for 0° C. In either scenario, the saturated scrubbing fluid 74 and liquid oxygenate product streams 78 are degassed in flashed drum 50 and light alcohols are partially separated from aldehydes and water in a stripper column 60. In another refinement, the scrubber uses hydrated formaldehyde as an absorbent to remove hydrogen sulfide and/or sulfur dioxide.

Advantageously, reactor 70 may incorporate a number of different processes which utilize the gaseous predominantly non-hydrocarbon stream 72, composed especially of nitrogen, hydrogen, carbon monoxide and/or carbon dioxide, for synthesis of more valuable products. These products include, but are not limited to, methanol, syngas or mixtures thereof, mixed alcohols or higher homolog alcohols, aldehydes, carboxylic acids and esters, carbonate esters, ammonia, etc. Some of these synthesis processes may also include the generated liquid products as reaction inputs.

Reaction conditions favoring the best selectivity for methanol and other oxygenates are as follows: The composition of the reaction mixture, after combining the heated hydrocarbon feed stream and the oxygen-containing feed stream, should be from about 1 mol % to about 10 mol % oxidant, preferably from about 2 mol % to about 5 mol % oxidant, and most preferably at about 2.5 mol % oxidant. The total pressure of the gases in the reactor system should be in the range of from about 5 MPa to about 10 MPa, preferably from about 5 MPa to about 9 MPa, and most preferably at about 8 Mpa. The reactor system wall temperature should be in the range of from about 600 K to about 900 K, and more preferably from about 723 K to about 823 K. The overall reactor residence time should be in the range of from about 1 second to about 40 seconds, more preferably from about 1 second to about 10 seconds, and most preferably from about 1 second to about 2.5 seconds.

For continuous operation, the fuel (e.g., natural gas) and oxidant are typically well-mixed. For this purpose a mixing chamber/reactor is supplied for both thoroughly mixing the reaction components and for also inducing the generation of alkyl (e.g., without limitation, methyl) free radicals that are then contained in the output stream from the mixing chamber. In this regard, the mixing chamber therefore effectively provides an injectively-mixed backmixing reaction chamber ("backmix reaction chamber") in a reactor system having an injectively-mixed backmixing reaction chamber in fluid communication with a tubular-flow reactor for carrying out the overall reaction. Details of a design that may be used to create such a backmixing chamber are set forth in U.S. Pat. Pub. No. 20070166212, the entire disclosure of which is hereby incorporated by reference. The injectively-mixed backmixing reaction chamber has a space-time, respective to a combined feed rate of the alkane-containing feed stream and the oxygen-containing feed stream, of from about 0.05 seconds to about 1.5 seconds (a preferably contemplated space-time is about 0.1 seconds) so that the feeds can be effectively mixed and so that an initial induction period for generating alkyl free radicals (e.g., without limitation, methyl free radicals) can be accommodated before the injectively-mixed backmixing reaction chamber product stream (methane, oxygen, and methyl free radicals) is fed to the tubular-flow reactor for further reaction into methanol.

In another variation, the design of the injectively-mixed backmixing reaction chamber enables injective intermixing of the alkane and oxygen-containing feed streams to turbulently agitate streams together and to effectively turbulently agitate the injectively-mixed backmixing reaction chamber. In this regard, the generating of methyl free radicals is perceived to be the first kinetic reaction step in the set of kinetic step reactions that achieve direct oxygenation of methane to methanol (one respective alkyl oxygenate), and the use of an injectively-mixed backmixing reaction chamber prior to the tubular-flow reactor enables a degree of freedom for independent optimization of this methyl free radical induction step. Other free radicals derived from C2-C4 alkanes should usually have a shorter induction period than the methyl free radical under comparable conditions. The subsequent chain branching kinetic sub-reactions (kinetic sub-reaction steps) then converts the methyl free radicals and other components of the injectively-mixed backmixing reaction chamber product stream to methanol and other products; these later sub-reactions are best controlled in the tubular-flow reactor environment that has traditionally received the admixed, but unreacted, methane (or other alkane) and oxygen of prior systems.

The reactor walls must be inert in the chemical environment of the reaction. The reactor construction material must be steel, preferably stainless steel, to contain the necessary total pressure. Insofar as a steel surface diminishes methanol selectivity, the steel is preferably coated with an inert coating, such as Teflon™, or an organic wax. Addition examples of coatings include, but are not limited to, Cotronics Resbond Ultra Temp 904 Zirconia Adhesive & Coating, Cerakote C-7300 Cerakote V-166, and the like. Insertion of a Pyrex™ or quartz sleeve into the reactor also provides a relatively inert surface.

In another embodiment, the flow restriction baffle (bulkhead with apertures for enabling a fluid passageway) is conveniently axially movable so that alternative baffle positions can be deployed in custom-configuring the effective space-time in the injectively-mixed backmixing reaction chamber prior to a process run instance or during a process run.

In another embodiment, the flow restriction baffle is further in close proximity to a blocking component that is conveniently axially movable so that variable baffle (bulkhead) passageways can be defined by partially blocking the apertures in the baffle (bulkhead) in custom-configuring the effective space-time in the injectively-mixed backmixing reaction chamber prior to a process run instance or during a process run; this feature provides another degree of freedom for operational control.

The methanol and other oxygenates can undergo thermal decomposition in the high temperatures of the tubular-flow reactor, resulting in product loss. Such decomposition is minimized by cooling of the reactor contents at a location immediately downstream from the "hot spot". Because wall cooling is not sufficiently responsive, a preferred embodiment employs injection of a cold gas by means of a tube whose axial position can also be changed by means of a sliding seal. The cold gas is preferably natural gas, but carbon dioxide, nitrogen, or another inert substance may also be used.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for preparing oxygenated hydrocarbons, comprising:
   a) supplying to a reactor a first heated hydrocarbon-containing gas stream;
   b) supplying separately to the reactor an oxygen-containing gas stream to form a reaction mixture, the oxygen-containing gas stream being prepared by passing air through one or more oxygen-enriching membranes to increase oxygen content, to partially oxidize the first heated hydrocarbon-containing gas stream in a partial oxidation reaction;
   c) separating and/or condensing one or more oxygenated hydrocarbons from a product stream;
   d) removing non-hydrocarbon gases from the product stream to enrich a gaseous hydrocarbon fraction using a scrubber and/or a hydrocarbon-enriching membrane; and
   e) mixing remaining gaseous hydrocarbon product from the product stream with a fresh first heated hydrocarbon-containing gas stream after one reaction cycle;
   wherein at least one membrane is used to increase oxygen content within step (b) and/or to remove non-hydrocarbon gases within step (d).

2. The method of claim 1, wherein within (b) one or more membranes are used to increase the oxygen content of the oxygen-containing gas stream entering the reactor.

3. The method of claim 2, wherein the oxygen-containing gas stream entering the reactor comprises between 20% and 100% oxygen.

4. The method of claim 2, wherein the oxygen-containing gas stream entering the reactor comprises less than 80% nitrogen.

5. The method of claim 2, wherein multiple membranes are used in series.

6. The method of claim 1, wherein within (d) the hydrocarbon-enriching membrane is used to remove non-hydrocarbon gases.

7. The method of claim 6, wherein, following separation of non-hydrocarbon gases using the hydrocarbon-enriching membrane, a resulting gas comprises a gaseous hydrocarbon fraction.

8. The method of claim 6, wherein the one or more gases including at least one of carbon monoxide, carbon dioxide, hydrogen and nitrogen.

9. The method of claim 1, wherein within (d) the hydrocarbon-enriching membrane and the scrubber are both used to remove non-hydrocarbon gases.

10. The method of claim 9, wherein the scrubber is used to remove carbon oxides.

11. The method of claim 1, wherein within (d) the hydrocarbon-enriching membrane, but not the scrubber, is used to remove non-hydrocarbon gases.

12. The method of claim 1, wherein one or more separated non-hydrocarbon gases are converted to a hydrocarbon which may be used as part of the first heated hydrocarbon-containing gas stream.

13. The method of claim 12, wherein the one or more separated non-hydrocarbon gases include carbon monoxide, carbon dioxide, and/or hydrogen.

14. The method of claim 1, wherein one or more separated non-hydrocarbon gases are converted to an oxygenated hydrocarbon product.

15. The method of claim 14 wherein the one or more separated non-hydrocarbon gases include carbon monoxide, carbon dioxide, and/or hydrogen.

16. The method of claim 1, further comprising supplying a second hydrocarbon-containing gas stream to the reactor downstream of the first heated hydrocarbon-containing gas stream and the oxygen-containing gas stream at a temperature below that of the first heated hydrocarbon-containing gas stream.

17. The method of claim 16, wherein the second hydrocarbon-containing gas stream is supplied to the reactor at a temperature of 0° C. to 100° C.

18. The method of claim 16, wherein the second hydrocarbon-containing gas stream is adjusted to mitigate decomposition of formaldehyde in the reactor.

19. The method of claim 18, wherein the temperature of the reaction mixture is reduced by at least 30° C. within a reaction vessel.

20. The method of claim 1, wherein the oxidation is partial oxidation without a catalyst, and wherein the mixture is substantially homogeneous.

21. The method of claim 1, wherein heat is transferred from the product stream to the first heated hydrocarbon-containing gas stream.

22. The method of claim 1, wherein oxidation occurs at pressures from about 5 to 9 MPA.

23. The method of claim 1, wherein oxidation is carried out in the reactor at a temperature between about 430° C. and 470° C.

24. The method of claim 1, wherein the first heated hydrocarbon-containing gas stream entering during a first cycle contains one or more non-hydrocarbon gases which may be removed by the scrubber and/or the hydrocarbon-enriching membrane following the partial oxidation reaction.

25. A system comprising:
a reactor;
a first hydrocarbon-containing gas supply means for supplying into the reactor a heated hydrocarbon-containing gas;
a means for supplying into the reactor an oxygen-containing gas;
one or more oxygen-enriching membranes to increase oxygen content of the oxygen-containing gas supplied into the reactor;
a means for separating and/or condensing one or more liquid oxygenated hydrocarbons from a product stream;
a scrubber and/or a hydrocarbon-enriching membrane to remove non-hydrocarbon gases from the product stream; and
a means for mixing remaining gaseous hydrocarbon product from the product stream with a fresh first heated hydrocarbon-containing gas stream after one reaction cycle, the system having at least one membrane.

26. The system of claim 25, comprising one or more membranes to increase oxygen content of the oxygen-containing gas supplied into the reactor.

27. The system of claim 26, comprising multiple membranes in series.

28. The system of claim 25, comprising the hydrocarbon-enriching membrane to remove non-hydrocarbon gases from the product stream.

29. The system of claim 28, further comprising a scrubber to remove carbon oxides from the product stream.

30. The system of claim 25, comprising one or more oxygen-enriching membranes to increase oxygen content of the oxygen-containing gas supplied into the reactor and the hydrocarbon-enriching membrane to remove non-hydrocarbon gases from the product stream.

31. The system of claim 25, also comprising a second hydrocarbon-containing gas supply means downstream of the heated hydrocarbon-containing gas and the oxygen-containing gas at a temperature below that of the heated hydrocarbon-containing gas.

32. The system of claim 25, including a heat exchange means for transferring heat from the product stream to the heated hydrocarbon-containing gas.

33. The system of claim 32, further comprising a heater disposed between the heat exchange means and the reactor for further preheating the heated hydrocarbon-containing gas prior to entry into the reactor.

34. The system of claim 25, further comprising a condenser that condenses a relatively low volatility component of the product stream for separation from a relatively high volatility component of the product stream.

35. A method of producing methanol, comprising:
supplying to a reactor a first heated hydrocarbon-containing gas stream;
supplying separately to the reactor an oxygen-containing gas stream, prepared by passing air through one or more membranes to increase oxygen content, to oxidize the first heated hydrocarbon-containing gas stream to form a product stream;
separating and condensing one or more oxygenated hydrocarbons including methanol from the product stream;
removing carbon monoxide and/or carbon dioxide from the product stream comprising one or more oxygenated hydrocarbons using a scrubber and a membrane; and
mixing remaining gaseous hydrocarbon product from the product stream with the first heated hydrocarbon-containing gas stream after one reaction cycle.

* * * * *